· US010299660B2

United States Patent
Hosogoe

(10) Patent No.: US 10,299,660 B2
(45) Date of Patent: May 28, 2019

(54) ENDOSCOPE HAVING A TREATMENT TOOL RAISING BASE

(71) Applicant: HOYA CORPORATION, Tokyo (JP)

(72) Inventor: Yoshitsugu Hosogoe, Tokyo (JP)

(73) Assignee: HOYA CORPORATION, Tokyo (JP)

( * ) Notice: Subject to any disclaimer, the term of this patent is extended or adjusted under 35 U.S.C. 154(b) by 204 days.

(21) Appl. No.: 14/992,264

(22) Filed: Jan. 11, 2016

(65) Prior Publication Data

US 2016/0206180 A1      Jul. 21, 2016

(30) Foreign Application Priority Data

Jan. 15, 2015  (JP) .................................. 2015-006084

(51) Int. Cl.
*A61B 1/00* (2006.01)
*A61B 8/00* (2006.01)
(Continued)

(52) U.S. Cl.
CPC ........ *A61B 1/00098* (2013.01); *A61B 1/0057* (2013.01); *A61B 1/00066* (2013.01);
(Continued)

(58) Field of Classification Search
CPC .............. A61B 1/0008; A61B 1/00087; A61B 1/00098; A61B 1/00131; A61B 1/00133;
(Continued)

(56) References Cited

U.S. PATENT DOCUMENTS 5,562,600 A    10/1996  Matsuno
6,605,033 B1 *  8/2003  Matsuno ............ A61B 1/00098
                                                        600/106
(Continued)

FOREIGN PATENT DOCUMENTS

CN      101073492      11/2007
JP      H11-151202 A    6/1999
(Continued)

OTHER PUBLICATIONS

Search Report issued by European Patent Office (EPO) patent office in European Patent Office (EPO) Patent Application No. 16150882.5, dated May 25, 2016.
(Continued)

*Primary Examiner* — Ryan N Henderson
(74) *Attorney, Agent, or Firm* — Greenblum & Bernstein, P.L.C.

(57) ABSTRACT

An endoscope includes a raising base rotatably installed in an insertion portion of the endoscope, a recess formed in the insertion portion, a flexible control wire which is movable along an axis thereof relative to said insertion portion, a link member provided in the recess and connecting one end of the control wire to the raising base, and a cover which is detachably attached to the insertion portion to close the recess. The link member includes a rotational shaft which is coaxial with a of rotational axis of the raising base, the rotational shaft provided in the recess to be irrotatable relative to the raising base and detachably connected to the raising base; and a connecting portion detachably and irrotatably connected to the rotational shaft in the recess, the one end of the control wire being connected to the connecting portion at a position offset from the rotational shaft.

9 Claims, 5 Drawing Sheets

(51) Int. Cl.
*A61B 8/08* (2006.01)
*A61B 8/12* (2006.01)
*A61B 1/005* (2006.01)
*A61B 1/018* (2006.01)
*A61B 10/04* (2006.01)

(52) U.S. Cl.
CPC ...... *A61B 1/00073* (2013.01); *A61B 1/00183* (2013.01); *A61B 8/0841* (2013.01); *A61B 8/12* (2013.01); *A61B 8/445* (2013.01); *A61B 10/04* (2013.01); *A61B 1/0011* (2013.01); *A61B 1/018* (2013.01); *A61B 8/4405* (2013.01); *A61B 8/4422* (2013.01)

(58) Field of Classification Search
CPC ..... A61B 1/005; A61B 1/0051; A61B 1/0052; A61B 1/0053; A61B 1/0055; A61B 1/0056; A61B 1/0057; A61B 1/0058; A61B 1/01; A61B 1/0607; A61B 1/273; A61B 1/2733; A61B 1/2736; A61B 1/2676; A61B 10/04; A61B 8/12; A61B 8/445
USPC .......................... 600/107, 127, 129, 139–152
See application file for complete search history.

(56) References Cited

U.S. PATENT DOCUMENTS

| | | | |
|---|---|---|---|
| 8,469,946 B2 | 6/2013 | Sugita | |
| 2003/0073955 A1* | 4/2003 | Otawara | A61B 1/00098 604/164.01 |
| 2004/0082836 A1* | 4/2004 | Hino | A61B 1/0008 600/170 |
| 2010/0145144 A1* | 6/2010 | Kitano | A61B 1/00098 600/107 |
| 2015/0173711 A1 | 6/2015 | Hiraoka | |

FOREIGN PATENT DOCUMENTS

| | | |
|---|---|---|
| JP | 2000-175864 A | 6/2000 |
| JP | 3527561 | 2/2004 |
| JP | 2007-330756 A | 12/2007 |
| WO | 2014/038638 | 3/2014 |

OTHER PUBLICATIONS

Office Action issued in China Counterpart Patent Appl. No. 201610028148.5, dated Apr. 24, 2017, along with an English translation thereof.

Office Action issued in Japan family member Patent Appl. No. 2015-006084, dated Mar. 20, 2018.

* cited by examiner

ENDOSCOPE HAVING A TREATMENT TOOL RAISING BASE

BACKGROUND OF THE INVENTION

1. Field of the Invention

The present invention relates to an endoscope having a treatment tool raising base which is manipulated to change the orientation of a treatment tool which is projected outwardly from the distal end of the insertion portion of the endoscope.

2. Description of the Related Art

Endoscopes provided, in the vicinity of the insertion portion thereof, with a treatment tool raising base that is rotatable are known in the art.

The endoscope disclosed in Japanese Patent Publication No. 3,527,561 is an example of such a type of endoscope. This endoscope is provided with a control portion and an insertion portion which extends from the control portion, and is further provided, at different positions on a surface of the insertion portion in the vicinity of the distal end of the insertion portion, with a raising base accommodation recess and a link member accommodation recess, respectively. The inner end of the link member accommodation recess (the opposite end thereof from the surface of the insertion portion) is communicatively connected with the link member accommodation recess.

This endoscope is further provided with a raising base which is accommodated in the raising base accommodation recess to be rotatable therein, a controller provided on the control portion, and a flexible control wire one end of which is connected to the controller and the other end of which is linked with the raising base. The entire control wire except the distal end thereof (the end of the control wire on the insertion portion side) is inserted into a wire guide conduit provided through the insertion portion and said control portion. The distal end of the control wire is positioned inside the link member accommodation recess.

The endoscope disclosed in Japanese Patent Publication No. 3,527,561 is further provided with a link member for linking the distal end of the control wire with the raising base. This link member is provided with a rotational shaft which extends along the axis of rotation of the raising base and is rotatable on its own axis, and a connecting portion which is connected to the outer end of the rotational shaft and extends orthogonal to the rotational shaft, and the rotational shaft and the connecting portion are formed integral with each other (i.e., non-separable from each other). Accordingly, the overall shape of the link member is in the shape of a substantially letter L.

Additionally, the inner end of the rotational shaft is connected to the raising base to be irrotatable relative to the raising base. The connecting portion of the link member is positioned in the link member accommodation recess, and the distal end of the control wire is connected to the connecting portion of the link member. The position of the connection of the control wire to the connecting portion is offset from the rotational shaft (in a radial direction of the rotational shaft).

Therefore, advancing and withdrawing the control wire along the axis thereof by manipulating the controller causes the link member to rotate forward and reverse about the rotational shaft, thus causing the raising base that is prevented from rotating relative to the rotational shaft (that rotates integrally with the rotational shaft) to rotate forward and reverse relative to the insertion portion.

This endoscope is further provided with a cover which is detachably attached to the insertion portion to close the link member accommodation recess in a watertight fashion so as to cover both the distal end of the control wire and the link member. Accordingly, even if the insertion portion of the endoscope is inserted into a body cavity of a test subject/patient with the cover attached to the insertion portion, there is little possibility of bodily fluids, etc., of the test subject/patient adhering to the control wire (the distal end thereof) or the link member.

Therefore, there is no need to wash either the control wire or the wire guide conduit when the endoscope is cleaned, which makes it possible to perform an endoscope cleaning operation easily (compared with an endoscope which has a structure that partly exposes the control wire and the wire guide conduit, thus requiring the control wire and the wire guide to be washed).

Although the link member accommodation recess is closed in a watertight manner by the cover, the watertight state with the cover cannot be said to be flawless. Accordingly, from the viewpoint of water-tightness, it is desirable that the dimensions of the link member accommodation recess (the area of the opening thereof on the surface of the insertion portion) be made as small as possible.

However, reducing the dimensions of the link member accommodation recess makes it difficult to install and remove the link member to and from the insertion portion (also to and from the raising base). Accordingly, the portion of the control wire which is positioned in the link member accommodation recess (i.e., the aforementioned distal end portion; hereinafter referred also to as the deformable portion) can be deformed (e.g., deformed in a direction sideways away from the insertion portion). However, in the case where the dimensions of the link member accommodation recess are small, the deformable portion of the control wire inevitably becomes small in length, so that the deformable amount of the deformable portion also becomes small; consequently, the degree of freedom in movement of the insertion portion (e.g., in the widthwise direction thereof) becomes small. Therefore, in the case where the length of the rotational shaft of the link member in the axial direction thereof is great, it is difficult to perform an insertion operation to insert the rotational shaft into the link member accommodation recess (and an operation to connect the rotational shaft to the raising base) and a removal operation to remove the rotational shaft from the link member accommodation recess (and an operation to disconnect the rotational shaft from the raising base).

SUMMARY OF THE INVENTION

The present invention provides an endoscope which is structured so that the link member can be easily installed into and removed from the insertion portion and the raising base, even in the case where the recess, which is formed on the surface of the insertion portion to accommodate both the link member (which links the control wire and the raising base to each other) and the end of the control wire (which is connected to the link member), is small and where the rotational shaft of the link member is long.

According to an aspect of the preset invention, an endoscope is provided, including a control portion; an insertion portion which extends from the control portion; a raising base which is installed in the insertion portion to be rotatable; a recess which is formed in the insertion portion at a different position from the raising base; a flexible control wire which is movable along an axis thereof relative to the insertion portion, one end of the control wire being positioned in the recess, wherein a part of the control wire that extends toward the control portion from the one end of the control wire is positioned inside the insertion portion; a link member which is provided in the recess and connects the one end of the control wire to the raising base; and a cover which is detachably attached to the insertion portion to close the recess, thereby covering the one end of the control wire and the link member. The link member includes a rotational shaft which is coaxial with an axis of rotation of the raising base, the rotational shaft being provided in the recess to be irrotatable relative to the raising base and to be detachably connected to the raising base; and a connecting portion which is detachably and irrotatably connected to the rotational shaft in the recess, the one end of the control wire being connected to a portion of the connecting portion at a position that is offset from the rotational shaft.

It is desirable for the recess to include a cover accommodation recess which is formed on a surface of the insertion portion, the cover being removably fitted into the cover accommodation recess; a connecting portion accommodation recess which is formed in a base surface of the cover accommodation recess and is spaced radially inwards from an inner peripheral surface of the cover accommodation recess, the connecting portion accommodation recess accommodating a portion of the rotational shaft and the connecting portion in a manner to allow the portion of the rotational shaft and the connecting portion to rotate in the recess; and a clearance groove which is formed in an inner peripheral surface of the connecting portion accommodation recess, an end of the connecting portion being positioned in the clearance groove when the connecting portion is located at a specific rotational position.

It is desirable for the cover to include a metal cover which closes the cover accommodation recess in a watertight manner.

It is desirable for a pair of female screw holes to be formed in the base surface of the cover accommodation recess at positioned spaced from each other in an axial direction of the insertion portion, wherein a pair of screws which pass through the metal cover are screw-engaged with the pair of female screw holes. The connecting portion accommodation recess includes a narrow portion which is smaller in size in the axial direction of the insertion portion than a remaining portion of the connecting portion accommodation recess. The narrow portion is positioned between the pair of female screw holes.

It is desirable for the connecting portion to be slidable relative to the rotational shaft in an axial direction thereof, wherein the endoscope further includes a first slide prevention portion which is formed at a middle portion of the rotational shaft and radially projects therefrom to prevent the connecting portion from sliding toward the raising base, and a second slide prevention portion which is formed on an inner surface of the metal cover to prevent the connecting portion from sliding toward an opposite side of the connecting portion from the raising base side at a position where the connecting portion does not come off the rotational shaft.

It is desirable for the cover to further include an exterior cover which closes the cover accommodation recess from outside of the metal cover. An outer surface of the exterior cover is flush with a surface of the insertion portion when the exterior cover is fitted into the cover accommodation recess The link member of the endoscope according to the present invention is structured so that the rotational shaft (which is provided in the recess of the insertion portion to be rotatable about the axis of rotation of the raising base, irrotatable relative to the raising base and detachably connected to the raising base) and the connecting portion (to which one end of the control wire is connected at a position that is offset from the rotational shaft) can be mutually connected and disconnected. Namely, the rotational shaft and the connecting portion can be independently connected and disconnected when the link member is installed onto and removed from the insertion portion (the recess) and the raising base. Therefore, even if the recess that is formed on a surface of the insertion portion is small and the rotational shaft of the link member is long, the rotational shaft (which is disengaged from the control wire) can be solely and easily detachably-fitted into the insertion portion (the recess) and the raising base.

In addition, the amount of movement of the connecting portion (the amount of deformation of the control wire) which is required to fit the connecting portion onto the rotational shaft is smaller than the amount of movement of the link member (the amount of deformation of the control wire) that is required to mount the link member (composed of the rotational shaft and the connecting portion which are integrally fixed to each other in a non-separable manner) to the insertion portion (the recess) and the raising base. Therefore, even if the recess that is formed on a surface of the insertion portion is small and the rotational shaft is long, the connecting portion (which is integral with the control wire) can be easily installed and removed to and from the rotational shaft.

The present disclosure relates to subject matter contained in Japanese Patent Application No. 2015-6084 (filed on Jan. 15, 2015) which is expressly incorporated herein by reference in its entirety.

BRIEF DESCRIPTION OF THE DRAWINGS

The present invention will be described below in detail with reference to the accompanying drawings in which.

DESCRIPTION OF THE EMBODIMENT

Figure 1:
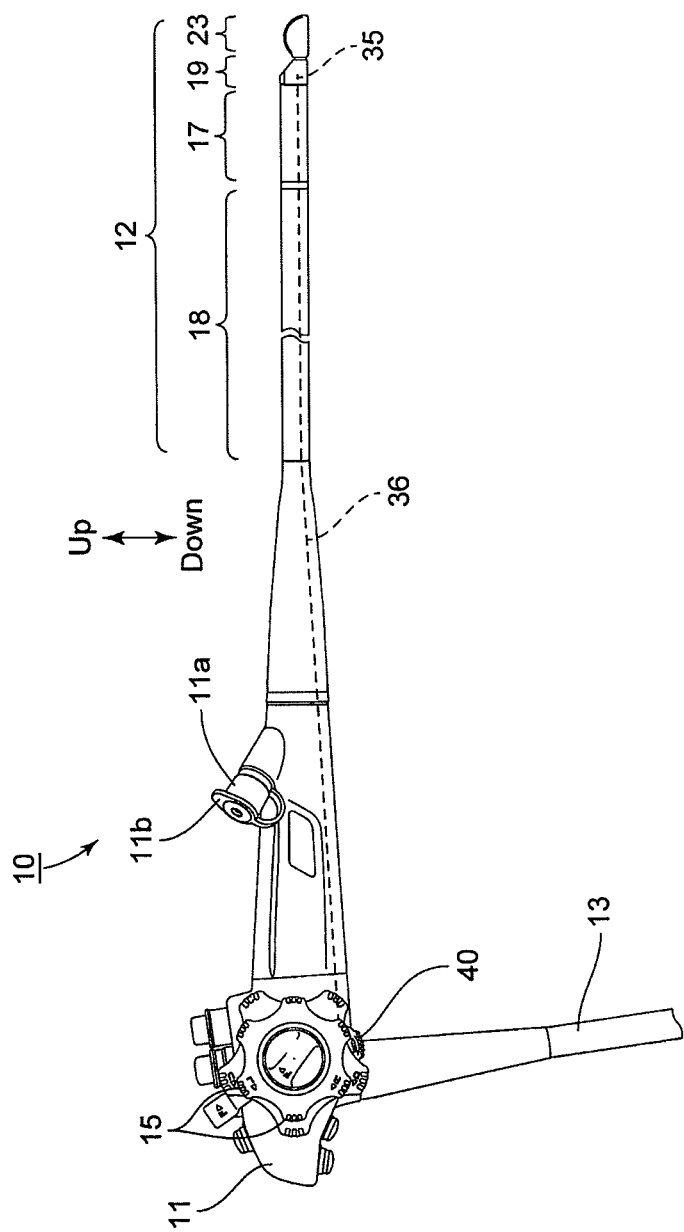
FIG. 1 is an external view of an embodiment of an ultrasonic endoscope according to the present invention.
Figure 2:
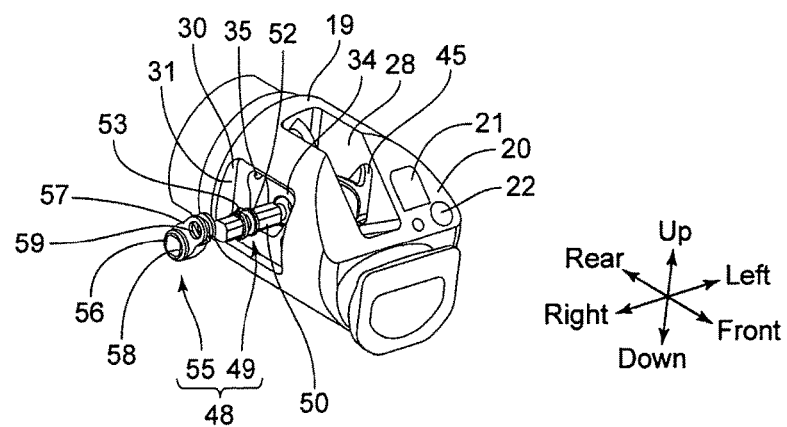
FIG. 2 is a perspective view of a distal-end rigid portion of the endoscope shown in FIG. 1, from which an ultrasonic probe is removed and in which a connecting portion and a rotational shaft are detached from each other, viewed from the front of the distal-end rigid portion.

An embodiment of an endoscope 10 according to the present invention will be hereinafter discussed with reference to FIGS. 1 through 9. In the following descriptions, forward and rearward directions, leftward and rightward directions, and upward and downward directions are determined with reference to the directions of the double-headed arrows shown in the drawings (the endoscope 10 is provided with an insertion portion 12 and a universal tube 13, and the distal end side of the insertion portion 12 and the distal end side of the universal tube 13 are defined as "front side" and "rear side", respectively).

The ultrasonic endoscope 10 shown in FIG. 1 is provided with a control portion 11, an insertion portion 12, a universal tube 13 and an ultrasonic image transmission tube (not shown). The insertion portion 12 extends forward from the control portion 11. The universal tube 13 and the ultrasonic image transmission tube extend from the control portion 11 in a different direction from the extending direction of the insertion portion 12. The ultrasonic image transmission tube is connected to an ultrasonic diagnostic apparatus (not shown) and the universal tube 13 is connected to a processor (not shown) (which serves as an image processor and a light source apparatus). The ultrasonic diagnostic apparatus and the processor are connected to a CRT monitor (not shown).

The insertion portion 12 is provided with a bending portion 17 which bends upward, downward, leftward and rightward in accordance with the rotating operation of a control knob 15 provided on the control portion 11. The portion of the insertion portion 12 which extends from the bending portion 17 toward the proximal end is formed as a flexible tube portion 18 which bends under its own weight or by a direct operation performed by the operator of the ultrasonic endoscope 10.

A portion of the insertion portion 12 in the vicinity of the distal end thereof includes a distal-end rigid portion 19 made of a hard resin. An inclined surface 20 is formed on the distal-end rigid portion 19. An object lens 21 and a lighting lens 22, etc., are provided on the inclined surface 20. An ultrasonic probe 23 which is connected to the front end surface of the distal-end rigid portion 19 constitutes the front end of the insertion portion 12. A ultrasonic wave signal cable 24 (see FIG. 9) which is flexible and the front end of which is connected to the ultrasonic wave probe 23 is provided through the insides of the insertion portion 12, the control portion 11 and the aforementioned ultrasonic image transmission tube.

Figure 9:
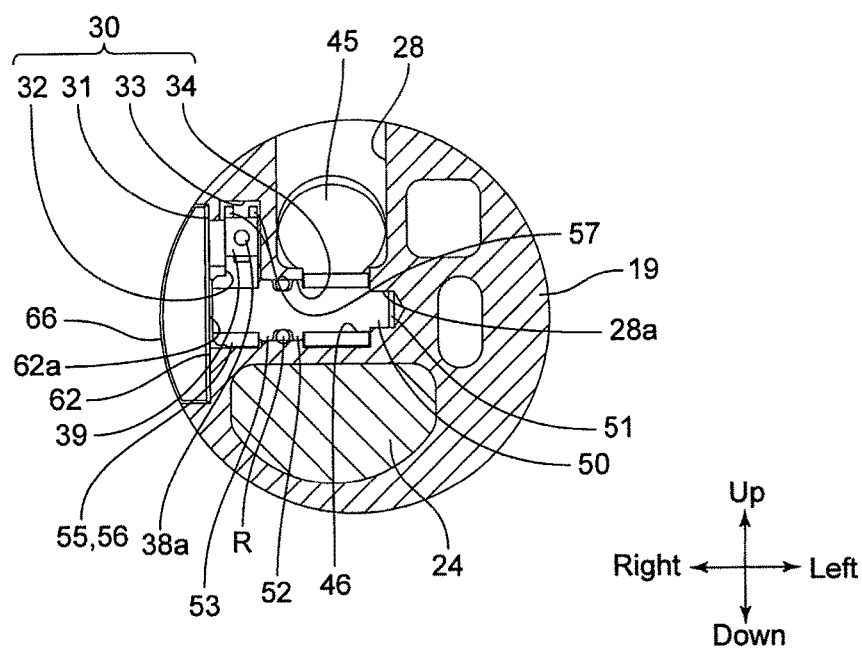
FIG. 9 is an enlarged cross sectional view taken along the line IX-IX shown in FIG. 8, viewed in the direction of the appended arrows.

As shown in FIG. 1, the control portion 11 is provided at the front end thereof with a tool insertion-opening protrusion 11a which protrudes obliquely and rearwardly. A flexible puncture needle (treatment tool) is inserted into (through) the tool insertion-opening protrusion 11a. A treatment tool insertion tube (not shown; a treatment tool insertion conduit) is provided inside the insertion portion 12 to extend from the tool insertion-opening protrusion 11a toward the distal-end rigid portion 19. The end opening of the tool insertion-opening protrusion 11a can be closed and opened with a rubber cap 11b. The distal-end rigid portion 19 is provided on the upper side thereof with a raising base accommodation recess 28 which is recessed downward. As shown in FIG. 9, the distal-end rigid portion 19 is provided, in the vicinity of the lower end of the left side (the right side with respect to FIG. 9) of the raising base accommodation recess 28, with a bearing recess 28a having a circular cross sectional shape which is recessed leftward (toward the right side with respect to FIG. 9). The distal end of the aforementioned treatment tool insertion tube is connected to the raising base accommodation recess 28 and allows the puncture needle which is inserted into the tool insertion-opening protrusion 11a to project into the raising base accommodation recess 28 from the end opening of the treatment tool insertion tube.

The distal-end rigid portion 19 is provided, on a side thereof at a different position from the raising base accommodation recess 28 in the circumferential direction of the distal-end rigid portion 19, with a link member accommodation recess (recess) 30. The link member accommodation recess 30 is provided with a cover accommodation recess 31, a connecting portion accommodation recess 32, a clearance groove 33 and a rotational shaft accommodation recess 34. The cover accommodation recess 31 is formed on a side (surface) of the distal-end rigid portion 19 and is substantially rectangular in a side view. The connecting portion accommodation recess 32 is formed in the base of the cover accommodation recess 31 and has a substantially trapezoidal shape in a side view. The clearance groove 33 is formed in an upper part of the inner peripheral surface of the connecting portion accommodation recess 32. The rotational shaft accommodation recess 34 is formed in the bottom of the connecting portion accommodation recess 32 to extend linearly toward the raising base accommodation recess 28 and to be coaxially with the bearing recess 28a.

As shown in the drawings, the connecting portion accommodation recess 32 is recessed to be spaced radially inwards from the inner peripheral surface of the cover accommodation recess 31. The lower end of the connecting portion accommodation recess 32 constitutes a narrow portion 32a which is smaller in size in the forward and rearward directions than the remaining part of the connecting portion accommodation recess 32. The link member accommodation recess 30 is provided, in the bottom of the cover accommodation recess 31 on both sides of the narrow portion 32a in the forward and rearward directions, with a front and rear pair of female screw holes 31a. The clearance groove 33 is smaller in width in the forward and rearward directions than the upper end portion of the connecting portion accommodation recess 32. Additionally, as shown in FIG. 9, the clearance groove 33 is spaced from the cover accommodation recess 31 toward the raising base accommodation recess 28 (the clearance groove 33 and the cover accommodation recess 31 are not directly communicatively-connected to each other). The left end of the rotational shaft accommodation recess 34 is communicatively connected with the raising base accommodation recess 28 (see FIG. 9).

The distal-end rigid portion 19 is provided therein with a cable insertion hole 35 which is formed as a through-hole extending in the forward and rearward directions. The front end opening of the cable insertion hole 35 is open at an upper rear side of the inner peripheral surface of the connecting portion accommodation recess 32, and the rear end opening of the cable insertion hole 35 is open at the rear end surface of the distal-end rigid portion 19 (see FIG. 6). The ultrasonic endoscope 10 is provided with a cable insertion tube 36 (see FIG. 1) which is formed as a flexible tube which extends through the inside the bending portion 17, the flexible tube portion 18 and the control portion 11. The front end of the cable insertion tube 36 is connected to the rear end of the cable insertion hole 35, and the rear end of the cable insertion tube 36 is positioned inside the control portion 11.

The ultrasonic endoscope 10 is provided, inside the cable insertion hole 35 and the cable insertion tube 36, with a metal flexible control wire 38 which is installed to be capable of being advanced and withdrawn in the axial direction of the control wire 38. As shown in FIG. 1, a raising base control lever 40 is rotatably mounted on the control portion 11. The inner end of the raising base control lever 40 is positioned in an internal space of the control portion 11, and the rear end of the control wire 38 that projects out of the rear end of the cable insertion tube 36 is connected to the inner end of the raising base control lever 40. On the other hand, the front end of the control wire 38 projects into the connecting portion accommodation recess 32 from the front end opening of the cable insertion hole 35. This front end of the control wire 38 that projects into the connecting portion accommodation recess 32 is designated by the reference numeral 38a in FIGS. 4, 5, 6 and 9. In addition, a metal cylindrical connecting pin 39 is fixed to the front end 38a of the control wire 38.

A metal raising base 45 is accommodated in the raising base accommodation recess 28. A rotational shaft connecting hole 46, having a substantially rectangular cross sectional shape (non-circular in cross section), is formed at the base end of the raising base 45 to extend therethrough in the leftward and rightward directions. The raising base 45 is accommodated in the raising base accommodation recess 28 so that the rotational shaft connecting hole 46 is coaxial with the bearing recess 28a and the rotational shaft accommodation recess 34.

A metal link member 48 is installed in the connecting portion accommodation recess 32 (the clearance recess 33), the rotational shaft accommodation recess 34 and the raising base accommodation recess 28 (the bearing recess 28a). The link member 48 is provided with a rotational shaft 49 and a connecting portion 55 which are provided as separate members and are capable of being connected and disconnected to and from each other.

The rotational shaft 49 is identical in cross-sectional shape to the rotational shaft connecting hole 46 of the raising base 45 (thus having a substantially rectangular cross-sectional shape) and is integrally provided with a shaft body 50, a shaft end portion 51, a first flange 52 and a second flange (first slide prevention portion) 53. The axis of the shaft body 50 extends in the leftward and rightward directions, the shaft end portion 51 is circular in cross section and projects from the left end surface of the shaft body 50, and the first flange 52 and the second flange 53 are projected radially outwards from the outer periphery of the shaft body 50 and are spaced from each other in the leftward and rightward directions (in the axial direction of the shaft body 50). The outer diameters of the first flange 52 and the second flange 53 are substantially identical to the inner diameter of the rotational shaft accommodation recess 34. Additionally, an O-ring R made of an elastic material is removably fitted on the outer periphery of the shaft body 50 to be positioned between the first flange 52 and the second flange 53 (see FIG. 9).

The connecting portion 55 is provided with a body portion 56 and a left and right pair of pin mounting lugs 57 which project radially outwards from the body portion 56. The body portion 56 is provided with a shaft connecting hole 58 which is formed through the body portion 56 in the leftward and rightward directions and has substantially the same cross-sectional shape as the shaft body 50 (specifically as the rotational shaft connecting hole 46). On the other hand, the left and right pair of pin mounting lugs 57 are provided with left and right pin mounting holes 59, respectively, which are formed to have substantially the same cross-sectional shape as the connecting pin 39 and are coaxial with each other (the pin mounting holes 59 are aligned in the leftward and rightward directions). As shown in the drawings, the position of the pair of pin mounting holes 59 is offset from the shaft connecting hole 58 (in a radial direction of the shaft connecting hole 58). The connecting pin 39, which is fixed to the front end 38a of the control wire 38, is press-fitted into the pin mounting holes 59 of the pair of pin mounting lugs 57, so that the control wire 38 and the connecting portion 55 are made integral with each other via the connecting pin 39.

When the link member 48 is installed into the connecting portion accommodation recess 32 (the clearance recess 33), the rotational shaft accommodation recess 34 and the raising base accommodation recess 28 (the bearing recess 28a), the rotational shaft 49 and the connecting portion 55 of the link member 48 are independently installed to these recesses 32 (33), 34 and 28(28a).

Figure 3:
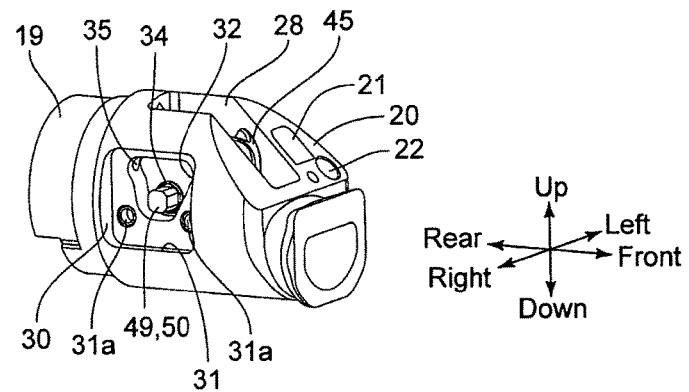
FIG. 3 is a perspective view similar to that of FIG. 2, showing a state where the rotational shaft is mounted to the distal-end rigid portion and a raising base provided in the distal-end rigid portion.

Specifically, first the rotational shaft 49 with the O-ring R integrally fitted thereon is inserted into the rotational shaft accommodation recess 34, the rotational shaft connecting hole 46 of the raising base 45 and the bearing recess 28a of the raising base accommodation recess 28 from the right end of the rotational shaft accommodation recess 34, as shown in FIGS. 3 and 9. More specifically, the shaft end portion 51 is fitted into the bearing recess 28a to be rotatable relative to the bearing recess 28a, a portion of the shaft body 50 is fitted into the rotational shaft connecting hole 46 to be irrotatable relative to the rotational shaft connecting hole 46 of the raising base 45, the first flange 52 and the second flange 53 are fitted into the rotational shaft accommodation recess 34 to be rotatable relative to the rotational shaft accommodation recess 34, and the portion of the shaft body 50 which extends from the second flange 53 rightward (the right end of the shaft body 50) is brought into the connecting portion accommodation recess 32 to be positioned therein. Thereupon, the rotational shaft 49 becomes rotatable about the axis thereof relative to the distal-end rigid portion 19 (relative to the bearing recess 28a and the rotational shaft accommodation recess 34), and accordingly, the raising base 45 (which is prevented from rotating relative to the rotational shaft 49 via the rotational shaft connecting hole 46 and the shaft body 50) is rotatable with the rotational shaft 49 (with the axis of rotation of the raising base 45) relative to the distal-end rigid portion 19. In other words, the raising base 45 is integral with the rotational shaft 49 and the rotational axis of the raising base 45 is coaxial with the rotational axis of the rotational shaft 49. Additionally, the O-ring R comes in contact with the entire inner periphery of the rotational shaft accommodation recess 34 in a watertight fashion while being elastically deformed.

Figure 4:
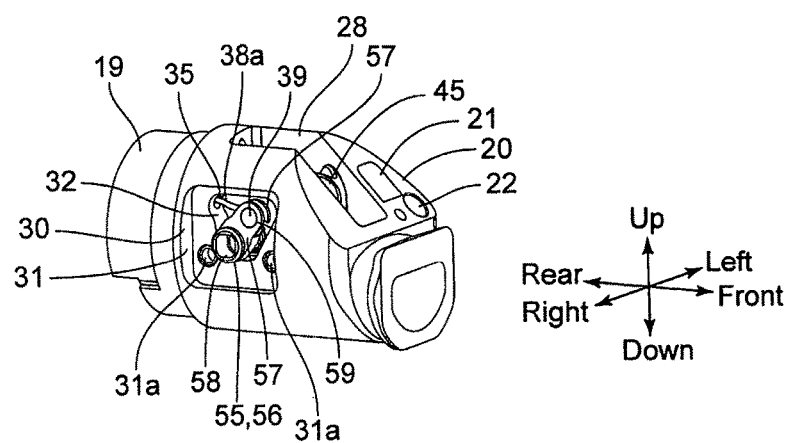
FIG. 4 is a perspective view similar to that of FIG. 2, showing a state where the connecting portion has been brought close to the rotational shaft.
Figure 5:
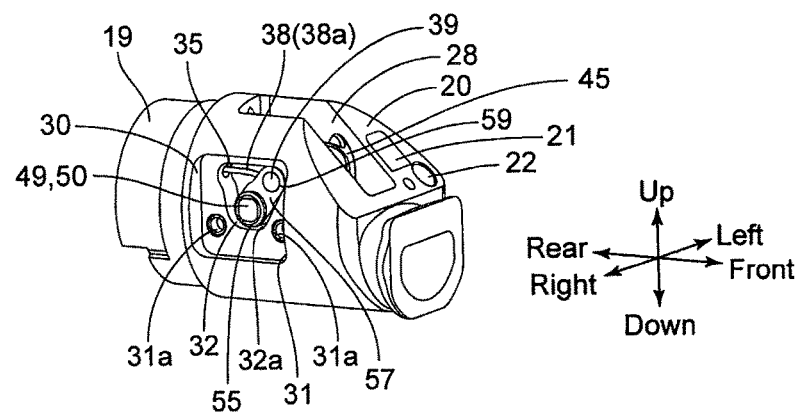
FIG. 5 is a perspective view similar to that of FIG. 2, showing a state where the connecting portion is connected to the rotational shaft.
Figure 6:
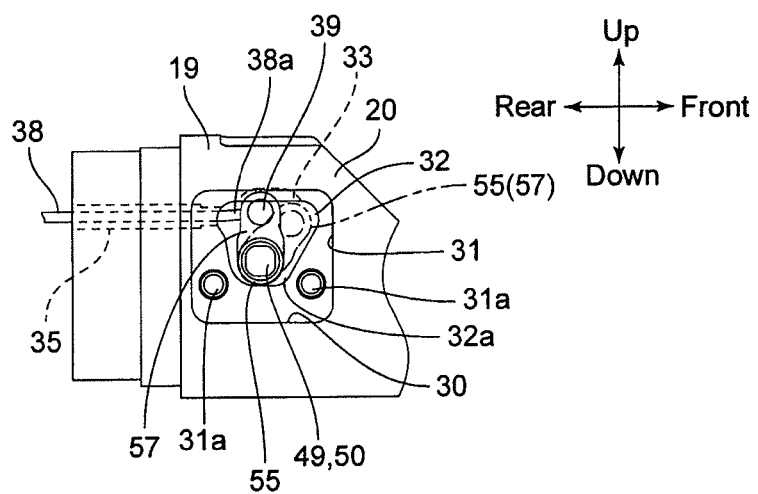
FIG. 6 is aside elevational view of the distal-end rigid portion in the state shown in FIG. 5.

Subsequently, the body portion 56 of the connecting portion 55 is brought close to the right end of the rotational shaft 49 while deforming (bending) the front end (deformable portion) 38a of the control wire 38 (see FIG. 4). Thereupon, the pair of pin mounting lugs 57 of the connecting portion 55 are held inclined forward with respect to the upward and downward directions (held to be substantially parallel to the front surface (front inclined surface) of the connecting portion accommodation recess 32). Subsequently, the body portion 56 of the connecting portion 55 is fitted onto the right end of the shaft body 50 in a manner to be irrotational relative to the shaft body 50 and to be slidable on the right end of the shaft body 50 in the axial direction of the rotational shaft 49 (see FIG. 5). Thereupon, the connecting portion 55 is entirely accommodated in the connecting portion accommodation recess 32, and the pair of pin mounting lugs 57 of the connecting portion 55 are positioned at the same position as the clearance groove 33 in the leftward and rightward directions (see FIGS. 5 and 9). Additionally, the connecting portion 55 is prevented from moving leftward relative to the shaft body 50 by engagement of the left end surface of the body portion 56 with the second flange 53 (which serves as the first slide prevention portion).

Connecting the connecting portion 55 to the rotational shaft 49 in the above described manner links the control wire 38 (the connecting pin 39) with the raising base 45 via the rotational shaft 49 and the connecting portion 55. Therefore, rotating the raising base control lever 40, which is provided on the control portion 11, in one rotation direction causes the control wire 38 to move rearward relative to the insertion portion 12 (relative to the cable insertion hole 35 and the cable insertion tube 36), thereby causing the connecting portion 55 (the pair of pin mounting lugs 57) to rotate rearward about the rotational shaft 49, as shown by solid lines in FIG. 6. Since the position of the pair of pin mounting holes 59 of the connecting portion 55 (the position of the connecting pin 39) is offset from the shaft connecting hole 58 of the body portion 56 in a radial direction of the rotational shaft 49 (in a radial direction of the shaft connecting hole 58), the rotational force (rotational torque) transmitted to the pair of pin mounting lugs 57 via the connecting pin 39 of the control wire 38 becomes great (compared with the case where the control wire 38 is connected directly to the body portion 56), and this rotational force is transmitted to the rotational shaft 49 and the raising base 45. Accordingly, the raising base 45 rotates in the rearward direction with a large torque.

On the other hand, rotating the raising base control lever 40 in the reverse direction causes the control wire 38 to move forward relative to the insertion portion 12 (relative to the cable insertion hole 35 and the cable insertion tube 36), thus causing the connecting portion 55 (the pair of pin mounting lugs 57) to rotate forward about the rotational shaft 49, thereby rotating the raising base 45 forward.

As shown in the drawings, the length of the connecting portion 55 is greater than the size of the connecting portion accommodation recess 32 in the upward and downward direction. However, a rearward rotation of the connecting portion 55 (the pair of pin mounting lugs 57) from the forwardly-inclined state (the state where the pair of pin mounting lugs 57 are substantially parallel to the front surface (front inclined surface) of the connecting portion accommodation recess 32) causes the radially outer ends of the pair of pin mounting lugs 57 to move into the clearance groove 33 (see FIGS. 6 and 9), so that the connecting portion 55 (the pair of pin mounting lugs 57) does not interfere with the inner surface of connecting portion accommodation recess 32 (the clearance groove 33) when rotating rearward from the forwardly inclined state.

Figure 7:
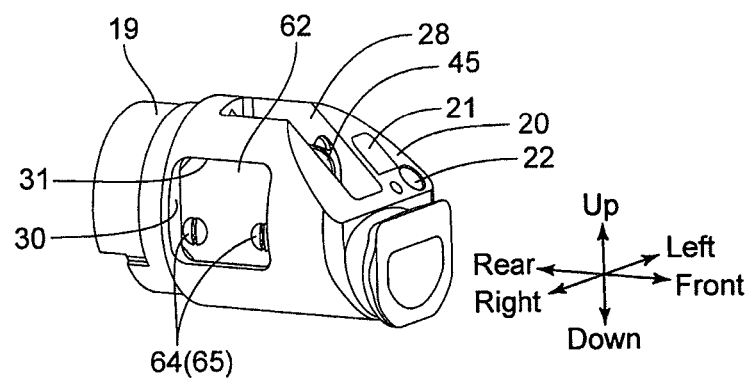
FIG. 7 is a perspective view similar to that of FIG. 2, showing a state where a metal cover is mounted to the distal-end rigid portion.

As shown in FIG. 7, a metal cover (cover) 62 is removably-fitted into the cover accommodation recess 31 of the link member accommodation recess 30 from the outside of the distal-end rigid portion 19 in a manner to cover the front end 38a of the control wire 38 and the link member 48.

The shape of the outer peripheral edge of the metal cover 62 is identical to the shape of the inner peripheral surface of the cover accommodation recess 31. Therefore, fitting the metal cover 62 into the cover accommodation recess 31 causes the outer peripheral edge of the metal cover 62 to come in watertight contact with the inner peripheral surface of the cover accommodation recess 31. In addition, two set screws 64 are inserted into two (front and rear) through-holes (not shown) formed in the metal cover 62, and the male thread portion (not shown) of each set screw 64 is screwed into the associated female screw hole 31a with the head 65 of the set screw 64 pressed against an outer surface of the metal cover 62. Accordingly, the metal cover 62 is fixed to the cover accommodation recess 31 (the connecting portion accommodation recess 32) with the two set screws 64.

Upon the metal cover 62 being fixed to the cover accommodation recess 31, a movement prevention surface (second slide prevention portion) 62a which is formed on the inner surface (the left side surface) of the metal cover 62 faces the right end surface of the shaft body 50 with a gap formed therebetween which is smaller (much smaller) than the width of the body portion 56 (the shaft connecting hole 58) in the leftward and rightward directions (see FIG. 9). Therefore, in the state where the metal cover 62 is fixed to the cover accommodation recess 31 as shown in FIG. 7, the engagement of the body portion 56 of the connecting portion 55 with the shaft body 50 cannot be released and the connecting portion 55 is prevented from coming off the right end of the shaft body 50.

Figure 8:
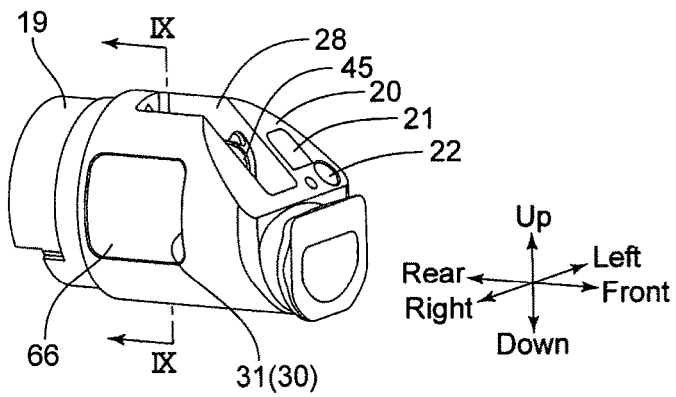
FIG. 8 is a perspective view similar to that of FIG. 2, showing a state where an exterior cover is mounted onto the distal-end rigid portion.

An exterior cover (cover) 66, made of a hard resin, is removably fitted into the cover accommodation recess 31 from the outside of the metal cover 62 (see FIG. 8). The shape of the outer peripheral edge of the exterior cover 66 is identical to the shape of the inner peripheral surface of the cover accommodation recess 31. In addition, the outer surface (right surface) of the exterior cover 66 has a curved shape that is flush with the outer peripheral surface of the distal-end rigid portion 19. Accordingly, fitting the exterior cover 66 into the cover accommodation recess 31 causes the outer surface of the exterior cover 66 to be flush with the outer peripheral surface of the distal-end rigid portion 19 (see FIG. 8).

The ultrasonic endoscope 10 that has the above described structure is used with the insertion portion 12 inserted into a body cavity of a test subject/ patient after the ultrasonic probe 23 is covered with a balloon (not shown) made of an elastic material (e.g., silicon rubber), and the space created between the ultrasonic probe 23 and this balloon is filled with water.

After the cap 11b is pulled off the tool insertion-opening protrusion 11a, if the tip of a puncture needle (treatment tool; not shown) is inserted into the aforementioned treatment tool insertion tube from the opening of the tool insertion-opening protrusion 11a and the puncture needle continues to be inserted, the tip of the puncture needle (treatment tool; not shown) projects forward from the front end opening of the treatment tool insertion tube. Thereupon, the puncture needle is supported, at the vicinity of the tip thereof, on the upper surface of the raising base 45. In this state, upon an ultrasonic wave being sent out from the ultrasonic probe 23, the ultrasonic wave reflected by the puncture needle is received by the ultrasonic probe 23, and the tip of the puncture needle is displayed as an ultrasonic wave image on the CRT monitor.

The raising base 45 rotates when the operator rotationally manipulates the raising base control lever 40 while monitoring the CRT monitor. This rotation of the raising base 45 causes the puncture needle to bend in the vicinity of the tip thereof, thereby changing the orientation of the tip of the puncture needle.

Accordingly, if the operator bends the puncture needle using the raising base 45 after the insertion portion 12 of the ultrasonic endoscope 10 is inserted into a body cavity of a test subject/ patient, various procedures using the puncture needle can be performed.

When an endoscopic examination using the ultrasonic endoscope 10 is performed on a test subject/ patient, bodily fluids adhere to the insertion portion 12 of the ultrasonic endoscope 10. Therefore, after the completion of the endoscopic examination, it is required to clean the ultrasonic endoscope 10 using a cleaning liquid, etc.

However, since the link member accommodation recess 30 (the cover accommodation recess 31) of the ultrasonic endoscope 10 is closed in a watertight manner by the metal cover 62 (and the exterior cover 66) and also since the O-ring R that is integrally fitted on the rotational shaft 49 comes in watertight contact with the entire inner peripheral surface of the rotational shaft accommodation recess 34, there is little possibility of bodily fluids, etc., that are adhered to the surface of the insertion portion 12 entering the side of the cover accommodation recess 31, the connecting portion accommodation recess 32 or the clearance groove 33 from the opening of the cover accommodation recess 31. Additionally, even if bodily fluids adhered to the raising base 45 and the right side of the raising base accommodation recess 28 enter the rotational shaft accommodation recess 34 from the left end opening thereof, there is little possibility of the bodily fluids entering beyond the right side of the O-ring R through a gap between the O-ring R and the inner surface of the rotational shaft accommodation recess 34. Accordingly, when the ultrasonic endoscope 10 is cleaned, it is not required to wash and clean the control wire 38 (the front end 38a thereof), the connecting portion 55 and the inner surfaces of the cover accommodation recess 31, the connecting portion accommodation recess 32 and the clearance groove 33 after the metal cover 62 and the exterior cover 66 are removed from the cover accommodation recess 31.

Further merits of the present embodiment of the ultrasonic endoscope 10 will be discussed hereinafter.

As shown in FIG. 9, the ultrasonic wave signal cable 24 is provided through a lower portion of the inside of the distal-end rigid portion 19, so that the raising base 45 and the connecting portion accommodation recess 32 are provided above the ultrasonic wave signal cable 24 to be prevented from interfering with the ultrasonic wave signal cable 24. Due to this structure, the area of the opening of the cover accommodation recess 31 of the link member accommodation recess 30 must be reduced in size (compared with the case where the raising base 45 and the connecting portion accommodation recess 32 are provided at the same position as the ultrasonic wave signal cable 24 in the upward and downward directions). Additionally, although the fitting of the metal cover 62 (and the exterior cover 66) into the cover accommodation recess 31 reduces the possibility of bodily fluids entering the side of the cover accommodation recess 31, the connecting portion accommodation recess 32 and the clearance groove 33 from the opening of the cover accommodation recess 31, the possibility of bodily fluids entering is likely to increase if the area of the opening of the cover accommodation recess 31 is large. Therefore, also from the viewpoint of an improvement in water-tightness of the cover accommodation recess 31, the area of the opening of the cover accommodation recess 31 needs to be reduced in size. However, if the area of the opening of the connecting portion accommodation recess 32 becomes small as a result of the cover accommodation recess 31 being reduced in size, the length of the front end 38a of the control wire 38 becomes short, which causes the deformable amount of the front end 38a of the control wire 38 to shorten. As a result, the degree of freedom in movement of the connecting portion 55, which is integral with the front end 38a of the control wire 38 via the connecting pin 39, relative to the distal-end rigid portion 19 (the link member accommodation recess 30) decreases.

However, since the connecting portion 55 (which is made integral with the control wire 38) and the rotational shaft 49 are provided as separate members in the present embodiment of the ultrasonic endoscope, even if the area of the link member accommodation recess 30 (the cover accommodation recess 31 and the connecting portion accommodation recess 32) that is formed on a surface of the distal-end rigid portion 19 is small and the length of the rotational shaft 49 of the link member 48 is long, the rotational shaft 49 (which is disengaged from the control wire 38) can be solely and easily fitted into the distal-end rigid portion 19 (the link member accommodation recess 30) and the raising base 45 (the rotational shaft connecting hole 46).

Additionally, the amount of movement of the connecting portion 55 (the amount of deformation of the front end 38a) which is required to fit the connecting portion 55 onto the rotational shaft 49 (the shaft body 50) is smaller than the amount of movement of the link member (composed of the rotational shaft 49 and the connecting portion 55 which are fixed integral with each other in a non-separable manner) which is required to mount the link member (the rotational shaft 49 thereof) to the distal-end rigid portion 19 (the link member accommodation recess 30) and the raising base 45 (the rotational shaft connecting hole 46). Therefore, even if the area of the link member accommodation recess 30 (the cover accommodation recess 31 and the connecting portion accommodation recess 32) that is formed on a surface of the distal-end rigid portion 19 is small and the length of the rotational shaft 49 of the link member 48 is long, the connecting portion 55 (which is integral with the control wire 38) can be easily installed onto and removed from the rotational shaft 49.

A similar merit is also obtained when the link member 48 (the rotational shaft 49 and the connecting portion 55) is detached from the distal-end rigid portion 19 (the link member accommodation recess 30) and the raising base 45 (the rotational shaft connecting hole 46). Specifically, when the link member 48 is detached from the distal-end rigid portion 19 (the link member accommodation recess 30) and the raising base 45 (the rotational shaft connecting hole 46), it is possible to easily detach only the connecting portion 55 which is integral with the control wire 38 via the connecting pin 39 from the rotational shaft 49 (which is fitted to the link member accommodation recess 30 and the raising base 45) and the rotational shaft 49 (which is disengaged from the control wire 38) can also be easily detached from the distal-end rigid portion 19 (the link member accommodation recess 30) and the raising base 45 (the rotational shaft connecting hole 46).

The narrow portion 32a, which is the smallest in size in the forward and rearward directions out of all the portions of the connecting portion accommodation recess 32, is positioned between the pair of female screw holes 31a. With this structure, the metal cover 62 can be firmly fixed with respect to the cover accommodation recess 31 (the connecting portion accommodation recess 32) by the two set screws 64 even with a reduced area of each opening of the cover accommodation recess 31 and the connecting portion accommodation recess 32.

Although the present invention has been described based on the above illustrated embodiment, the present invention is not limited solely thereto; various modifications to the above illustrated embodiment are possible without departing from the scope of the invention.

For instance, the shaft connecting hole 58 of the connecting portion 55 can be replaced by a recess, the right end of which being closed.

In addition, it is possible to form a projection on the connecting portion 55 side, to form a depression (or a through-hole) on the right end surface of the rotating shaft 49 so that the depression is engaged with the aforementioned projection to be irrotational relative to the aforementioned projection, and to disconnectably connect the rotational shaft 49 and the connecting portion 55 to each other via the engagement of the aforementioned projection with the aforementioned depression (or the aforementioned through-hole).

The clearance groove 33 can be omitted if the size of the connecting portion accommodation recess 32 in the upward and downward directions is made greater than the length of the connecting portion 55, when oriented in the upward and downward directions.

Each of the raising base 45 and the link member 48 can be formed from a material other than metal.

Although the above illustrated embodiment discloses the ultrasonic endoscope 10 to which the present invention has been applied, the present invention can also be applied to an endoscope which is not equipped with an ultrasonic probe such as the ultrasonic probe 23 (i.e., the present invention can also be applied to a normal endoscope having no function using ultrasound).

Additionally, any treatment tool other than a puncture needle (e.g., an imaging catheter or a baby scope) can also be used as a treatment tool (having flexibility) which is bent by using the raising base 45.

Obvious changes may be made in the specific embodiment of the present invention described herein, such modifications being within the spirit and scope of the invention claimed. It is indicated that all matter contained herein is illustrative and does not limit the scope of the present invention.

What is claimed is:

1. An endoscope comprising:
   a control portion;
   an insertion portion which extends from said control portion;
   a raising base which is provided in said insertion portion so as to be rotatable;
   a recess which is provided in said insertion portion at a position spaced from said raising base;
   a flexible control wire which is movable along an axis thereof relative to said insertion portion, one end of said control wire being positioned in said recess, a part of said control wire that extends toward said control portion from said one end of said control wire, is positioned within said insertion portion;
   a linkage which is provided in said recess and connects said one end of said control wire to said raising base; and
   a cover which is detachably attached to said insertion portion to close said recess, thereby covering said one end of said control wire and said linkage,
   wherein said linkage includes a rotational shaft which is coaxial with an axis of rotation of said raising base, said rotational shaft being provided in said recess to be irrotatable relative to said raising base and to be detachably connected to said raising base, and a connecting portion which is detachably and irrotatably connected to said rotational shaft in said recess, said one end of said control wire being connected to a portion of said connecting portion at a position that is offset from said rotational shaft, wherein said rotational shaft of said linkage and said connecting portion of said linkage are distinct from each other,
   said connecting portion is slidable relative to said rotational shaft in an axial direction thereof,
   wherein said endoscope further comprises:
   a slide preventer provided at a middle portion of said rotational shaft and radially projects therefrom to prevent said connecting portion from sliding toward said raising base, said slide preventer comprises an outwardly extending flange that projects from the intermediate portion of said rotational shaft.

2. The endoscope according to claim 1, wherein said recess comprises:
   a cover accommodation recess which is provided on a surface of said insertion portion, said cover being removably fitted into said cover accommodation recess;
   a connecting portion accommodation recess which is provided in a base surface of said cover accommodation recess and is spaced radially inwards from an inner peripheral surface of said cover accommodation recess, said connecting portion accommodation recess accommodating a portion of said rotational shaft and said connecting portion so as to allow said portion of said rotational shaft and said connecting portion to rotate in said recess; and
   a clearance groove which is provided in an inner peripheral surface of said connecting portion accommodation recess, an end of said connecting portion being positioned in said clearance groove when said connecting portion is located at a specific rotational position.

3. The endoscope according to claim 2, wherein said cover comprises a metal cover which closes said cover accommodation recess in a watertight manner.

4. The endoscope according to claim 3, wherein a pair of screw holes are provided in said base surface of said cover accommodation recess at positions spaced from each other in an axial direction of said insertion portion,
   wherein a pair of screws which pass through said metal cover are screw-engaged with said pair of screw holes,
   wherein said connecting portion accommodation recess includes a narrow portion which is smaller in size, in said axial direction of said insertion portion, than a remaining portion of said connecting portion accommodation recess, and
   wherein said narrow portion is positioned between said pair of screw holes.

5. The endoscope according to claim 3,
   wherein said endoscope further comprises:
   a second slide preventer which is provided on an inner surface of said metal cover to prevent said connecting portion from sliding toward an opposite side of said connecting portion from said raising base side at a position where said connecting portion does not come off said rotational shaft.

6. The endoscope according to claim 3, wherein said cover further comprises an exterior cover which closes said cover accommodation recess externally of said metal cover,
   wherein an outer surface of said exterior cover is flush with a surface of said insertion portion when said exterior cover closes said cover accommodation recess.

7. The endoscope according to claim 1, the rotational shaft and the connecting portion are connectable and disconnectable from each other.

8. An endoscope comprising:
   a control portion;
   an insertion portion which extends from said control portion;
   a raising base which is mounted in said insertion portion so as to be rotatable;
   a recess provided in said insertion portion at a position spaced from a position of said raising base;
   a flexible control wire which is axially movable with respect to said insertion portion, one end of said control wire being positioned in said recess, a portion of said control wire that extends towards said control portion from said one end of said control wire, is positioned within said insertion portion;

a linkage provided in said recess and connecting said one end of said control wire to said raising base;

a cover detachably attachable to said insertion portion to close said recess, thereby covering said one end of said control wire and said linkage;

said linkage including a rotational shaft which is coaxial with an axis of rotation of said raising base, said rotational shaft being provided in said recess so as to be irrotatable relative to said raising base and to be detachably connected to said raising base and a connecting portion which is detachably and irrotatably connected to said rotational shaft in said recess, said one end of said control wire being connected to a portion of said connecting portion at a position that is offset from said rotational shaft, said connecting portion being slidable relative to said rotational shaft in an axial direction thereof, a first slide preventer provided at an intermediate portion of said rotational shaft and radially projecting from said rotational shaft to prevent said connecting portion from sliding towards said raising base, said first slide preventer comprises an outwardly extending flange that projects from the intermediate portion of said rotational shaft; and a second slide preventer provided on an inner surface of a metal cover that closes said recess to prevent said connecting portion from sliding towards a side of said connecting portion opposite said raising base, at a position where said connecting portion does not come off said rotational shaft.

9. The endoscope according to claim 8, said second slide preventer comprising a movement prevention surface provided on an inwardly facing surface of said metal cover and configured to prevent the connecting portion from becoming disengaged from the rotational shaft.

* * * * *